United States Patent [19]

Zehnder

[11] Patent Number: 4,699,652
[45] Date of Patent: Oct. 13, 1987

[54] FUNGICIDAL PYRIDINE DERIVATIVES FOR USE IN AGRICULTURE

[75] Inventor: Beat Zehnder, Reinach, Switzerland

[73] Assignee: Hoffmann-La Roche Inc., Nutley, N.J.

[21] Appl. No.: 885,368

[22] Filed: Jul. 14, 1986

[30] Foreign Application Priority Data

Jul. 22, 1985 [CH] Switzerland .................. 3177/85
May 22, 1986 [CH] Switzerland .................. 2065/86

[51] Int. Cl.$^4$ .................. A01N 43/40; C07D 213/60; C07D 405/02; C07D 405/06
[52] U.S. Cl. .................. 71/94; 546/338; 546/334; 546/344; 546/268; 546/283
[58] Field of Search .............. 546/338, 334, 344, 268, 546/283; 71/94

[56] References Cited

FOREIGN PATENT DOCUMENTS 2104890  3/1983  United Kingdom ................ 546/344

*Primary Examiner*—Henry R. Jiles
*Assistant Examiner*—J. Richter
*Attorney, Agent, or Firm*—Jon S. Saxe; George M. Gould; Norman C. Dulak

[57] ABSTRACT

The invention is directed to fungicidal pyridine derivatives and their N-amino salts and acid addition salts, said pyridine derivatives having the formula

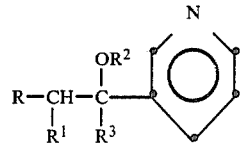

wherein R˙ is mono-, di- or trisubstituted phenyl, wherein the substituents are the same or different and are selected from the group consisting of 1 to 3 halogen, 1 or 2 $C_{1-3}$-alkyl, 1 or 2 $C_{1-3}$-alkoxy and 1 or 2 trifluoromethyl moieties; $R^1$ is hydrogen, $C_{1-6}$-alkyl, $C_{2-6}$-alkenyl or $C_{2-6}$-alkynyl; $R^2$ is hydrogen; $R^3$ is selected from the group consisting of —CO—$R^4$, —C(O$R^5$)=CH$R^6$, —CH($R^4$)O$R^5$, —C($R^4$)=NO$R^7$ and

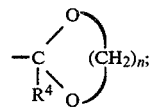

$R^4$ is hydrogen or $C_{1-5}$-alkyl; $R^5$ is $C_{1-4}$-alkyl; $R^6$ and $R^7$ are hydrogen or $C_{1-4}$-alkyl; n is 2 or 3; or $R^2$ taken together with $R^4$ is equal to the group —CH=CH— (vinylene); as well as to fungicidal compositions containing these compounds as the active substance, and to the use of the fungicidal pyridine derivatives, their N-amino salts and their acid addition salts in a method of combatting the growth of fungi in agriculture and in horticulture.

28 Claims, No Drawings

FUNGICIDAL PYRIDINE DERIVATIVES FOR USE IN AGRICULTURE

SUMMARY OF THE INVENTION

The invention is directed to novel pyridine derivatives which have fungicidal activity, and to compositions containing the novel pyridine derivatives of the invention as the active fungicidal agent, as well as to a method of combating phytopathogenic fungi which comprises applying to a plant, plant part, or soil in which the plant is growing or in which the plant is to be grown, a fungicidally effective amount of the compounds of the invention. The pyridine derivatives of the invention have the formula:

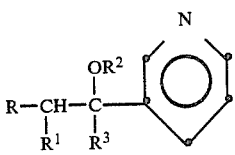
I wherein R is mono-, di- or trisubstituted phenyl independently substituted by halogen atoms or $C_{1-3}$-alkyl, $C_{1-3}$-alkoxy or trifluoromethyl groups; $R^1$ is hydrogen, $C_{1-6}$-alkyl, $C_{2-6}$-alkenyl or $C_{2-6}$-alkynyl; $R^2$ is hydrogen; $R^3$ is selected from the group consisting of —CO—$R^4$, —C(O$R^5$)=CH$R^6$, —CH($R^4$)O$R^5$, —C($R^4$)=NO$R^7$ and

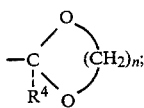

$R^4$ is hydrogen or $C_{1-5}$-alkyl; $R^5$ is $C_{1-4}$-alkyl; $R^6$ and $R^7$ equal hydrogen or $C_{1-4}$-alkyl; n is 2 or 3; $R^2$ together with $R^4$ may equal the group —CH=CH—, as well as the N-amino salts and acid addition salts of the compounds of formula I.

DETAILED DESCRIPTION OF THE INVENTION

The present invention is concerned with heterocyclic compounds, namely pyridine derivatives of the general formula

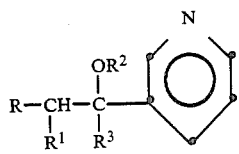
I wherein R is mono-, di- or trisubstituted phenyl, wherein the substituents are the same or different and are selected from the group consisting of 1 to 3 halogen atoms, 1 or 2 $C_{1-3}$-alkyl groups, 1 or 2 $C_{1-3}$-alkoxy groups and 1 or 2 trifluoromethyl groups; $R^1$ is hydrogen, $C_{1-6}$-alkyl, $C_{2-6}$-alkenyl or $C_{2-6}$alkynyl; $R^2$ is hydrogen; $R^3$ is selected from the group consisting of —CO—$R^4$, —C(O$R^5$)=CH$R^6$, —CH($R^4$)O$R^5$, —C($R^4$)=NO$R^7$ and

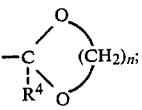

$R^4$ is hydrogen or $C_{1-5}$-alkyl; $R^5$ is $C_{1-4}$-alkyl; $R^6$ and $R^7$ are hydrogen or $C_{1-4}$-alkyl; n is 2 or 3; $R^2$ taken together with $R^4$ may equal the group —CH=CH—; and the N-amino salts and acid addition salts thereof.

The compounds of formula I and their N-amino salts and acid addition salts have fungicidal properties and are suitable as fungicidal active substances, especially for use in agriculture and in horticulture. The invention is also directed to fungicidal compositions which contain such compounds as the active substance, as well as to the use of such compounds and compositions for the control of fungi in agriculture and in horticulture.

In formula I above the term "halogen" refers to fluorine, chlorine, bromine and iodine atoms. The alkyl, alkenyl and alkynyl groups can be straight-chain or branched, and this also applies to the alkyl part of the alkoxy group. In di- or trisubstituted phenyl the substituents can be the same or different.

The term "N-amino salts" refers to compounds of formula I, wherein the 3-pyridyl group is modified in accordance with the following formula:

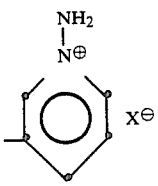

wherein $X^\oplus$ is an anion of a physiologically compatible acid.

Examples of such acids are alkanecarboxylic acids, benzoic acid and its ring-substituted derivatives such as, for example, alkyl-, nitro- and/or chloro-substituted benzoic acids, optionally substituted benzenesulphonic acid, carbamic acid, hydrochloric acid, hydrobromic acid, hydroiodic acid and sulphuric acid.

As acid addition salts of the compounds of formula I there come into consideration physiologically compatible salts. Hereto there belong preferably salts of these compounds with inorganic and organic acids such as hydrochloric acid; nitric acid; phosphoric acid; mono- and bifunctional carboxylic acids and hydroxycarboxylic acids, e.g. acetic acid, maleic acid, succinic acid, fumaric acid, tartaric acid, citric acid, salicylic acid, sorbic acid and lactic acid; and sulphonic acids, e.g. 1,5-naphthalene-disulphonic acid.

The presence of at least one asymmetric carbon atom in the compounds in accordance with the invention means that the compounds can occur as optical antipodes. Geometric isomerism can also occur by virtue of the presence of a possible aliphatic C=C or C=N double bond. Formula I is intended to embrace all of these possible isomeric forms and their mixtures.

Preferred for use herein are compounds of formula I wherein, independently, R is mono-, di- or trihalophenyl, especially 2,4-dichlorophenyl, $R^1$ is hydrogen or $C_{1-6}$-alkyl, $R^2$ is hydrogen and $R^3$ is —CO$R^4$ or —C(O$R^5$)=CH$R^6$, especially acetyl or 1-methoxy- or 1-ethoxyvinyl. Preferred for use herein are the free pyridine derivatives and their acid addition salts. Still another preferred group of compounds in accordance with the invention are those in which $R^1$ is hydrogen. A further preferred group of compounds of the invention are those formed when $R^1$ in formula I is methyl.

Especially preferred compounds of formula I are:

5-(2,4-Dichlorophenyl)-4-hydroxy-4-(3-pyridyl)-3-pentanone, 2-(2,4-dichloro-α-methylbenzyl)-2-(3-pyridyl)-3(2H)-furanone, 2-(2,4-dichlorobenzyl)-2-(3-pyridyl)-3(2H)-furanone, 4-(2,4-dichlorophenyl)-3-hydroxy-3-(3-pyridyl)-2-pentanone, 4-(2,4-dichlorophenyl-3-hydroxy-3-(3-pyridyl)-2-butanone, 4-(p-chlorophenyl)-3-hydroxy-3-(3-pyridyl)-2-pentanone, α-(2,4-dichlorobenzyl)-α-(1-methoxyvinyl)-3-pyridinemethanol, α-ethoxymethyl-α-(2,4-dichloro-α-methylbenzyl)-3-pyridinemethanol, α-(2,4-dichloro-α-methylbenzyl)-α-methoxymethyl-3-pyridinemethanol, α-(2,4-dichlorobenzyl)-α-(1-methoxyethyl)-3-pyridinemethanol, α-(2,4-dichlorobenzyl)-3-pyridineglycol aldehyde O-methyl oxime and α-(2,4-dichloro-α-methylbenzyl)-α-[(methoxyimino)-methyl]-3-pyridinemethanol.

Further representatives of compounds of formula I are:

3-(2,4-Dichlorophenyl)-2-hydroxy-2-(3-pyridyl)-1-butanone ethylene ketal,

α-(1-ethoxyethyl)-α-(2,4-dichlorobenzyl)-3-pyridinemethanol,

α-(2,4-dichloro-α-methylbenzyl)-α-(1-methoxyethyl)-3-pyridinemethanol,

α-(1-ethoxyethyl)-α-(2,4-dichloro-α-methylbenzyl)-3-pyridinemethanol,

α-(2,4-dichlorobenzyl)-α-(1-methoxy-2-methylpropyl)-3-pyridinemethanol,

α-(2,4-dichlorobenzyl)-α-methoxymethyl-3-pyridinemethanol and

α-ethoxymethyl-α-(2,4-dichlorobenzyl)-3-pyridinemethanol.

The process in accordance with the invention for the manufacture of the compounds of formula I and of their N-amino salts and acid addition salts comprises (a) for the manufacture of those compounds of formula I in which $R^2$ signifies hydrogen, $R^3$ signifies —$COR^4$ and $R^4$ signifies hydrogen or $C_{1-5}$-alkyl, subjecting a dithiane derivative of the general formula

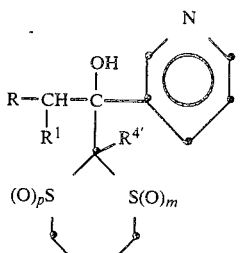

wherein R and $R^1$ are as defined in formula I, $R^{4'}$ is hydrogen or $C_{1-5}$-alkyl and p and m each independently equal 0 or 1, to a hydrolysis in acidic medium;

(b) for the manufacture of those compounds of formula I in which $R^3$ is —$COR^4$ and $R^4$ is $C_{1-5}$-alkyl or together with $R^2$ —CH=CH— (vinylene), subjecting an alkyne of the general formula

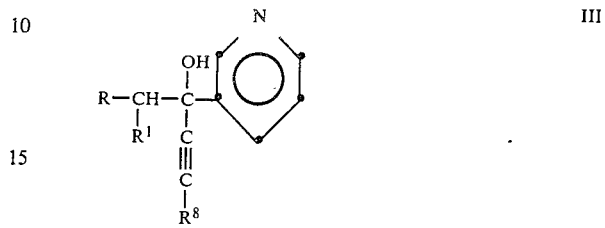

wherein R and $R^1$ are as defined in formula I, $R^8$ is hydrogen, $C_{1-4}$-alkyl or —$CH(OR^9)_2$ and $R^9$ is a lower alkyl residue, especially $C_{1-4}$-alkyl, to a hydrolysis in acidic medium;

(c) for the manufacture of those compounds of formula I in which $R^3$ is —$C(OR^5)$=$CHR^6$, reacting a ketone of the general formula

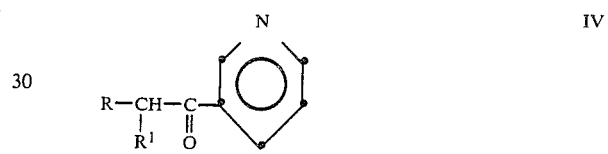

wherein R and $R^1$ are as defined in formula I, with a suitable metal salt, especially the lithium salt, of an enol ether of the general formula

wherein $R^5$ and $R^6$ are as defined in formula I;

(d) for the manufacture of those compounds of general formula I in which $R^2$ is hydrogen, $R^3$ is —$COR^4$ and $R^4$ is $C_{1-5}$-alkyl, subjecting an enol ether of the general formula

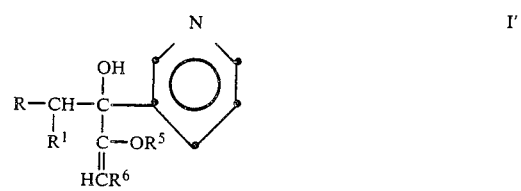

wherein R, $R^1$, $R^5$ and $R^6$ are as defined in formula I, to a hydrolysis in acidic medium;

(e) for the manufacture of those compounds of formula I in which $R^3$ is —$CH(R^4)OR^5$, treating an alcohol of the general formula

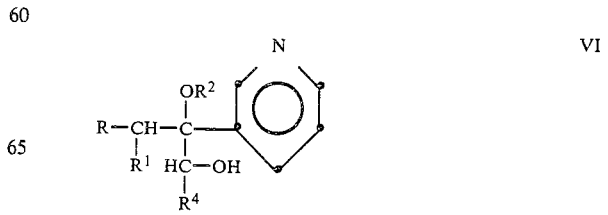

wherein R, $R^1$, $R^2$ and $R^4$ are as defined in formula I, with an alkylating agent;

(f) for the manufacture of those compounds of formula I in which $R^2$ is hydrogen, $R^3$ is —CH($R^4$)$OR^5$ and $R^4$ is $C_{1-5}$-alkyl, catalytically hydrogenating an enol ether of general formula I' given above;

(g) for the manufacture of those compounds of formula I in which $R^2$ is hydrogen, $R^3$ is —CH($R^4$)$OR^5$ and $R^4$ is $C_{1-5}$-alkyl, reacting a ketone of general formula IV given above with a suitable metal salt, especially the lithium salt, of a dialkyl ether of the general formula $$R^{4''}CH_2OR^5 \qquad \qquad VII$$

wherein $R^{4''}$ is $C_{1-5}$-alkyl and $R^5$ is as defined in formula I;

(h) for the manufacture of those compounds of formula I in which $R^3$ is —C($R^4$)=$NOR^7$, reacting an aldehyde or a ketone of the general formula

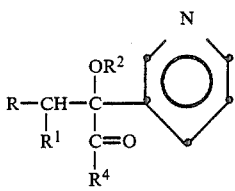

I'' wherein R, $R^1$, $R^2$ and $R^4$ are as defined in formula I, with an amine of the general formula $$H_2N—OR^7 \qquad \qquad VIII$$

wherein $R^7$ is as defined in formula I, or with a salt of this amine with a strong acid;

(i) for the manufacture of those compounds of formula I in which $R^3$ is

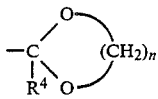

reacting an aldehyde or a ketone of general formula I' given above with ethylene glycol or propanediol-1,3 -and, for the manufacture of an N-amino salt of a compound of formula I, N-aminating the compound of formula I with an amine derivative of the general formula $$H_2N—X \qquad \qquad IX$$

in which $X^\ominus$ signifies the anion of a physiologically compatible acid, and, for the manufacture of an acid addition salt of a compound of formula I, reacting the compound of formula I with an acid.

Process variant (a) is conveniently carried out by hydrolyzing the dithiane derivative of formula II in dilute aqueous mineral acid, preferably 2–20% sulphuric acid, at temperatures between room temperature and the reflux temperature of the reaction mixture. In many cases it has been found to be advantageous to carry out the hydrolysis additionally in the presence of a catalytic amount of a heavy metal salt, e.g. of mercuric sulphate. When a dithiane derivative of formula II in which $R^1$ signifies $C_{2-6}$-alkynyl is hydrolyzed, the hydrolysis is carried out under mild reaction conditions, because the starting material is an "oxidated" dithiane derivative, i.e. p and m in formula II signify 1.

Process variant (b) is conveniently effected under the reaction conditions described above in connection with process variant (a), although in the case of an alkyne of formula III in which $R^8$ signifies —CH($OR^9$)$_2$ relatively mild reaction conditions are indicated and an addition of a heavy metal salt is to be avoided.

The enol ether addition according to process variant (c) is conveniently carried out by adding the ketone of formula IV to the metal salt, especially to the lithium salt, of the enol ether of formula V in an inert diluent, preferably an aprotic organic solvent such as an aliphatic or cyclic ether, e.g. diethyl ether, tetrahydrofuran or dioxan, in a temperature range of about −80° C. to 0° C. and leaving the mixture to react. In many cases it has been found to be advantageous to use the metal salt in excess, namely up to 200 mol percent. The salt is conveniently produced in situ prior to the addition of the ketone, for example by slowly adding tert.butyl lithium in an organic solvent, preferably a hydrocarbon, e.g. n-hexane, to a solution of the enol ether of formula V in the same solvent in which thereafter the reaction with the ketone IV is effected and at low temperatures, namely in the lower region of the above-mentioned temperature range. Thereafter, in order to accelerate the reaction, the température of the reaction mixture can be increased slowly, for example to about 0° C., and subsequently the mixture can be cooled and the ketone IV added thereto.

The hydrolysis according to process variant (d) is conveniently carried out by treating the enol ether of formula I' in a polar organic diluent such as a cyclic ether, e.g. tetrahydrofuran or dioxan, a lower aliphatic amide, e.g. dimethylformamide, or a lower alkanol, e.g. methanol, ethanol or isopropanol, with aqueous acid such as hydrochloric acid, sulphuric acid or trifluoroacetic acid at temperatures between 0° C. and the reflux temperature of the reaction mixture.

The etherification according to process variant (e) is conveniently carried out using a $C_{1-4}$-alkyl chloride, bromide, iodide, mesylate or tosylate or a di($C_{1-4}$-alkyl) sulphate as the alkylating agent in a diluent and in the presence of a base. The diluent is preferably a polar aprotic organic solvent such as an aliphatic or cyclic ether, e.g. dimethoxyethane or tetrahydrofuran, or a dialkylamide, e.g. dimethylformamide, and the base is preferably a strong base such as sodium hydride, calcium hydride or lithium diisopropylamide. The alcohol of formula VI can also be reacted with the alkylating agent in a two-phase mixture of an aqueous alkali metal hydroxide such as sodium hydroxide solution and a halogenated hydrocarbon such as methylene chloride or chloroform by means of a phase transfer catalyst, e.g. tetrabutylammonium hydrogen sulphate. In either case the reaction is conveniently effected at temperatures between 0° C. and the reflux temperature of the reaction mixture.

The hydrogenation according to process variant (f) is conveniently carried out using palladium or platinium as the catalyst, whereby the catalyst is suitably supported on an inert carrier such as calcium carbonate or active carbon. Moreover, the hydrogenation is conveniently carried out in the presence of an organic diluent. As such diluents there come into consideration especially lower alkanols, e.g. methanol and ethanol; aliphatic carboxylic acids, e.g. acetic acid; aliphatic ketones, e.g. acétone and 2-butanone; halogenated aliphatic hydrocarbons, e.g. methylene chloride and chloroform; and aromatics, e.g. toluene and xylenes. The hydrogenation is conveniently effected in a temperature range of 0° C. up to the reflux temperature of the reaction mixture and under a hydrogen pressure of one or more atmospheres.

The enol ether addition according to process variant (g) is conveniently carried out by adding the ketone of formula IV to the metal salt, especially to the lithium salt, of the dialkyl ether of formula VII in an inert diluent, preferably in an aprotic organic solvent such as an aliphatic or cyclic ether, e.g. tetrahydrofuran, dioxan or the same dialkyl ether VII, in a temperature range of about −100° C. up to room temperature, preferably at about −75° C., and leaving the mixture to react. It has been found to be advantageous to produce the metal salt in situ prior to the addition of the ketone IV, for example by treating the dialkyl ether VII with a strong base such as an alkyl lithium compound, optionally with the addition of an alcoholate such as potassium tert.butylate and/or an alkali metal halide such as lithium bromide, at low temperatures, namely in the lower range of the above-mentioned temperature interval. The ketone IV is thereupon added. A symmetric dialkyl ether VII or a dialkyl ether VII in which $R^5$ signifies tert.butyl is preferably used in this process variant.

The oxime formation according to process variant (h) is conveniently effected in a polar organic diluent such as a lower alkanol, e.g. methanol or ethanol; a dialkylamide, e.g. dimethylformamide; or a tertiary amine, e.g. pyridine, at temperatures between 0° C. and the reflux temperature of the reaction mixture. Where the amine of formula VIII is used in the form of an acid addition salt, e.g. the hydrochloride or hydrogen sulphate, a base such as sodium or potassium carbonate, triethylamine or pyridine is conveniently added to the reaction mixture unless the diluent used is itself basic.

The ketalization according to process variant (i) is conveniently carried out in an organic diluent, in the presence of an acid and in a temperature range between 80° C. and 140° C. Especially suitable diluents are aromatic hydrocarbons, e.g. benzene, toluene and xylenes. Such diluents permit, in particular, the continuous distillative removal from the reaction mixture of the water which is formed. As acids there come into consideration especially mineral acids such as sulphuric acid and hydrochloric acid or sulphonic acids such as p-toluenesulphonic acid. The dialcohol is preferably used in excess.

The N-amination of a compound of formula I with an amine derivative of formula IX is conveniently carried out by treating the compound I with the amine derivative in an inert organic diluent such as a halogenated aliphatic hydrocarbon, e.g. methylene chloride or chloroform, at temperatures between 0° C. and the reflux temperature of the reaction mixture.

For the manufacture of the acid addition salts of the compounds of formula I, the compounds I or their N-oxides are reacted with the desired acids in the usual manner.

The isolation and purification of the thus-manufactured compounds of formula I and of their N-amino salts and acid addition salts can be effected according to methods known per se.

The dithiane derivatives of formula II which are used as starting materials in process variant (a) are novel and can be produced by reacting a ketone of general formula IV given above with a dithiane salt of the general formula

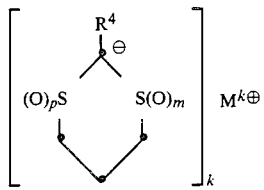

wherein $R^4$, p and m have the significances given above, $M^{k\oplus}$ is an alkali metal or alkaline earth metal cation and k is the valency of the cation M.

The alkali metal or alkaline earth metal is preferably lithium, sodium or potassium; or calcium or magnesium, respectively. The reaction is conveniently effected using an inert organic diluent, especially an aprotic organic solvent such as an aliphatic or cyclic ether, e.g. diethyl ether, tetrahydrofuran or dioxan, in a temperature range of about −80° C. to 0° C. In many cases it has been found to be advantageous to use the dithiane salt of formula X in excess, preferably up to 200 mol percent.

The starting materials of formulae III and IV are either known or can be produced according to methods known per se (see e.g. European Patent Publication No. 137,456). The starting materials or intermediates of formulae V and VII–X are also known or can be produced according to methods known per se.

The alcohols of formula VI which are used as starting materials in process variant (e) are novel and can be produced by reducing an aldehyde or a ketone of general formula I" given above. The reduction is preferably effected by means of a complex metal hydride such as sodium borohydride, in which case it is carried out in a protic organic diluent such as an alcohol, e.g. methanol or ethanol, or an aliphatic carboxylic acid, e.g. acetic acid, at temperatures about room temperature, or lithium aluminum hydride which is usually used in an aprotic organic diluent, especially an aliphatic or cyclic ether, e.g. diethyl ether, tetrahydrofuran or dioxan, at temperatures between 0° C. and room temperature. Lithium borohydride in ethanol or tetrahydrofuran, sodium borohydride-aluminium chloride in an ether, e.g. diglyme, and lithium tri(tert.butoxy)aluminium hydride in tetrahydrofuran also come into consideration as complex metal hydrides in suitable diluents. The aldehyde or the ketone of formula I" can also be reduced e.g. by means of diborane in tetrahydrofuran or by means of catalytic hydrogenation known per se, in which case an optionally halogenated hydrocarbon is usually used as the diluent. The reaction conditions for the respective reduction of the aldehyde or ketone I" are generally known to the person skilled in the art from analogous reductions.

These alcohols of formula VI form a further object of the present invention.

The starting materials of formula I' and I" are subgroups of the compounds of formula I: the enol ethers of formula I' can be produced in accordance with process variant (c) from corresponding ketones of formula IV and metal salts of the enol ethers of formula V, and the aldehydes or ketones of formula I" can be produced in accordance with process variants (a), (b) and (d) from corresponding dithiane derivatives of formula II, alkynes of formula III or enol ethers of formula I'.

The compounds in accordance with the invention, i.e. the compounds of formula I and their N-amino salts and acid addition salts, have fungicidal activity and can accordingly be used for the control of fungi in agriculture, in horticulture as well as in wood processing. They are especially suitable for inhibiting the growth or for the irradication of phytopathogenic fungi on parts of plants, e.g. leaves, stems, roots, tubers, fruits or flowers, and on seeds as well as in the soil. Further, wood-destroying and wood-discoloring fungi can be controlled with the compounds in accordance with the invention. The compounds in accordance with the invention are especially effective in the control of fungi of the classes Deuteromycetes, Ascomycetes and Basidiomycetes such as, for example, *Botrytis cinerea, Erysiphe cichoracearum, Erysiphe graminis, Uncinula necator, Podosphaera leucotricha, Venturia inaequalis, Cercospora archidicola, Cercospora beticola* and *Mycosphaerella fijiensis* as well as of harmful fungi of the genera Sphaerotheca, Puccinia, Uromyces, Hemileia, Rhizoctonia, Alternaria, Cercosphorella, Ceratocystis (e.g. *Ceratocystis ulmi* and *Ceratocystis fimbriata*), Verticullium, Fusarium, Helmithosporium, Sclerotinia, Penicillium, Septona, Ustilago, Tilletia, Coniophora, Gloeophyllum and Aureobasidium.

The compounds in accordance with the invention are distinguished by local and/or systemic activity.

The compounds in accordance with the invention are active against phytopathogenic fungi under greenhouse conditions even at concentrations of 1 mg to 500 mg of active substance per liter of spray liquor. In the open, concentrations of 25 g to 1500 g of active substance of formula I per hectare and treatment are advantageously used. For the control of seed- or soil-borne fungi in a disinfecting process there are advantageously used 0.05 g to 1.5 g of active substance of formula I per kg of seeds.

The compounds in accordance with the invention can be formulated to give a wide variety of compositions, e.g. solutions, suspensions, emulsions, emulsifiable concentrates and pulverous preparations. The fungicidal compositions in accordance with the invention contain an effective amount of at least one compound of general formula I, as defined above, or an N-amino salt or acid addition salt of such a compound as well as formulation adjuvants. The compositions conveniently contain at least one of the following formulation adjuvants:

Solid carrier substances; solvents or dispersion media; tensides (wetting and emulsifying agents); dispersing agents (without tenside action); and stabilizers.

As solid carrier substances there essentially come into consideration: natural mineral substances such as kaolin, aluminas, siliceous earth, talc, bentonite, chalk, e.g. whiting, magnesium carbonate, limestone, quartz dolomite, attapulgite, montmorillonite and diatomaceous earth; synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as granulates or powders.

As solvents or dispersion media there essentially come into consideration: aromatics such as toluene, xylenes, benzene and alkylnaphthalenes, chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents or dispersion media preferably having flash points of at least 30° C. and boiling points of at least 50° C., and water. Among the solvents or dispersion media there also come into consideration so-called liquefied gaseous extenders or carrier substances, these being products which are gaseous at room temperature and under normal pressure. Examples of such products are especially aerosol propellants such as halogenated hydrocarbons, e.g. dichlorodifluoromethane. When water is used as the solvent, organic solvents can e.g. also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alchols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzenesulphonates, e.g. calcium dodecylbenzenesulphonate, and butylnaphthalenesulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside activity) there essentially come into consideration: lignin, sodium and ammonium salts of lignin sulphonic acids, sodium salts of maleic anhydride-diisobutylene copolymers, sodium and ammonium salts of sulphonated polycondensation products from naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxyltoluene; UV-absorbers, e.g. substituted benzophenones, diphenylacrylonitrile acid esters and cinnamic acid esters; and deactivators, e.g. salts of ethylenediaminetetraacetic acid and polyglycols.

The fungicidal compositions in accordance with the invention can contain, in addition to the active substances of formula I, other active substances, e.g. other fungicidal agents, insecticidal and acaricidal agents, bactericides, plant growth regulators and fertilizers. Such combination compositions are suitable for broadening the spectrum of activity or for specifically influencing the plant growth.

The fungicidal compositions in accordance with the invention generally contain, according to type, between 0.0001 and 95 weight percent of compound in accordance with the invention or compounds in accordance with the invention as the active substance(s). They can be present in a form which is suitable for storage and transport. In such forms, e.g. emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 95 weight percent, preferably 25 to 75 weight percent, of the compound or compounds of formula I. As forms of use there come into consideration, inter alia, ready-for-use solutions, emulsions and suspensions which are suitable, for example, as spray liquors. In such spray liquors there can be present e.g. concentrations between 0.0001 and 20 weight percent. In the Ultra-Low-Volume process spray liquors can be formulated in which the active substance concentration is preferably from 0.5 to 20 weight percent, while the spray liquors formulated in the Low-Volume process and in the High-Volume process preferably have an active substance concentration of 0.02 to 1.0 and 0.002 to 0.1 weight percent, respectively.

The fungicidal compositions in accordance with the invention can be manufactured by mixing at least one compound of general formula I or an N-amino salt or acid addition salt of such a compound with formulation adjuvants.

The manufacture of the compositions can be carried out in a known manner, e.g. by mixing the active substance with solid carrier substances, by dissolution for suspension in suitable solvents or dispersion media, if necessary with the use of tensides as wetting or emulsifying agents or of dispersing agents, by diluting pre-prepared emulsifiable concentrates with solvents or dispersion media etc.

In the case of pulverous compositions the active substance can be mixed with a solid carrier substance, e.g. by grinding them together; or the solid carrier substance can be impregnated with a solution or suspension of the active substance and then the solvent or dispersion medium can be removed by evaporation, heating or by sucking-off under reduced pressure. By adding tensides or dispersing agents such pulverous compositions can be made readily wettable with water, so that they can be converted into aqueous suspensions which are suitable e.g. as spray compositions.

The compounds in accordance with the invention can also be mixed with a tenside and a solid carrier substance to form a wettable powder which is dispersible in water or they can be mixed with a solid pre-granulated carrier substance to form a product in the form of a granulate.

When desired, a compound in accordance with the invention can be dissolved in a water-immiscible solvent such as, for example, an alicyclic ketone, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obrained emulsifiable concentrates or ready-for-use emulsions.

The use of the compositions in accordance with the invention can be carried out according to the application methods which are usual in plant protection or in agriculture. The method in accordance with the invention for the control of fungi comprises treating the locus to be protected, e.g. plants, parts of plants or seeds, with an effective amount of a compound in accordance with the invention or of a composition in accordance with the invention.

Certain compounds of formula VI also have fungicidal activity and can be used for the control of fungi in agriculture, in horticulture as well as in wood processing analogously to the compounds of formula I and their N-amino salts and acid addition salts. Such compounds VI also have a similar spectrum of activity as the compounds of formula I, N-amino salts and acid addition salts and can be formulated to give a wide variety of fungicidal compositions and can be used just as these compounds.

The following compounds of formula VI are preferred on the basis of their especially pronounced fungicidal activity:

4-(2,4-Dichlorophenyl)-3-(3-pyridyl)-2,3-butanediol,
1-(2,4-dichlorobenzyl)-1-(3-pyridyl)-1,2-ethanediol,
5-(2,5-dichlorophenyl)-4-(3-pyridyl)-3,4-hexanediol,
3-(2,4-dichlorophenyl)-2-(3-pyridyl)-1,2-butanediol,
4-(2,4-dichlorophenyl)-3-(3-pyridyl)-6-heptyne-2,3-diol,
4-(2,4-dichlorophenyl)-3-(3-pyridyl)-6-heptene-2,3-diol and
4-(2,4-dichlorophenyl)-3-(3-pyridyl)-2,3-hexanediol.

The first four compounds VI are especially preferred fungicidal active substances.

The following Examples illustrate the invention.

I. MANUFACTURE OF THE ACTIVE SUBSTANCES OF FORMULA I

Example 1

180 mg of mercuric sulphate are added to a solution of 4.4 g of α-(2,4-dichlorobenzyl)-α-(2-isopropyl-m-dithianyl-2)-3-pyridinemethanol in 60 ml of 4N sulphuric acid and the reaction mixture is then heated at reflux temperature for 8 hours. The mixture is left to cool to room temperature, adjusted to pH 8 by the addition of solid sodium bicarbonate and partitioned between ethyl acetate and water. The organic phase is washed three times with saturated aqueous sodium chloride solution and evaporated under reduced pressure. The residue is subjected to a column chromatography on silica gel using diethyl ether as the eluent; it is crystallized from methylene chloride/n-hexane and there are thus obtained 3.0 g of 5-(2,4-dichlorophenyl)-4-hydroxy-2-methyl-4-(3-pyridyl)-3-pentanone, m.p. 144°–145° C.

In an analogous manner, starting from

α-(2-ethyl-m-dithianyl-2)-α-(2,4-dichloro-α-methylbenzyl)-3-pyridinemethanol there is obtained 1-(2,4-dichloro-α-methylbenzyl)-1-hydroxy-1-(3-pyridyl)-2-butanone as colorless crystals, m.p. 143.5°–144° C.;

α-(2-ethyl-m-dithianyl-2)-α-(2,4-dichlorobenzyl)-3-pyridinemethanol there is obtained 5-(2,4-dichlorophenyl)-4-hydroxy-4-(3-pyridyl)-3-pentanone as colorless crystals, m.p. 145°–146.5° C.;

α(2,4-dichloro-α-methylbenzyl)-α-(m-dithianyl-2)-3-pyridinemethanol there is obtained α(2,4-dichloro-α- methylbenzyl)-α-hydroxy-3-pyridineacetaldehyde as a colorless oil;

α-(2,4-dichlorobenzyl)-α-(m-dithianyl-2)-3-pyridinemethanol there is obtained α-(2,4-dichlorobenzyl)-α-hydroxy-3-pyridineacetaldehyde as a colorless oil.

Example 2

A solution of 1 g of α-(3,3-diethoxy-1-propynyl)-α-(2,4-dichloro-α-methylbenzyl)-3-pyridinemethanol in 30 ml of 4N sulphuric acid is heated at 120° C. for 1.5 hours while stirring and the reaction mixture is subsequently left to cool to room temperature, neutralized with solid sodium bicarbonate and extracted with methylene chloride. The organic phase is washed three times with saturated aqueous sodium chloride solution and evaporated under reduced pressure. Thereafter, the residue is subjected to a column chromatography on silica gel using methylene chloride/ethyl acetate (4:1) as the eluent and it is recrystallized from n-hexane. In this manner there is obtained 0.4 g of 2-(2,4-dichloro-α-methylbenzyl)-2-(3-pyridyl)-3(2H)-furanone, m.p. 111°-111.5° C.

In an analogous manner, starting from

α-(3,3-diethoxy-1-propynyl)-α-(2,4-dichlorobenzyl)-3-pyridinemethanol there is obtained 2-(2,4-dichlorobenzyl)-2-(3-pyridyl)-3(2H)-furanone, m.p. 129°-131° C.;

α-ethynyl-α-(2,4-dichloro-α-methylbenzyl)-3-pyridinemethanol there is obtained 4-(2,4-dichlorophenyl)-3-hydroxy-3-(3-pyridyl)-2-pentanone as colorless crystals, m.p. 147° C.;

α-ethynyl-α-(2,4-dichlorobenzyl)-3-pyridinemethanol there is obtained 4-(2,4-dichlorophenyl)-3-hydroxy-3-(3-pyridyl)-2-butanone as colorless crystals, m.p. 116.5°-118.5° C.;

α-(ethynyl)-α-(2,4-dichloro-α-propylbenzyl)-3-pyridinemethanol there is obtained 4-(2,4-dichlorophenyl)-3-hydroxy-3-(3-pyridyl)-2-heptanone as yellowish crystals, m.p. 133°-135° C.;

α-(3,3-diethoxy-1-propynyl)-α-(2,4-dichloro-α-propylbenzyl)-3-pyridinemethanol there is obtained 2-(2,4-dichloro-α-propylbenzyl)-2-(3-pyridyl)-3-(2H)-furanone as orange colored crystals, m.p. 112°-114° C.;

α-(ethynyl)-α-(p-chlorobenzyl)-3-pyridinemethanol there is obtained 4-(p-chlorophenyl)-3-hydroxy-3-(3-pyridyl)-2-butanone as colorless crystals, m.p. 114.5°-117.5° C.;

α-ethynyl-α-(p-chloro-α-methylbenzyl)-3-pyridinemethanol there is obtained 4-(p-chlorophenyl)-3-hydroxy-3-(3-pyridyl)-2-pentanone as colorless crystals, m.p. 104.5°-106.5° C.;

α-(p-chloro-α-methylbenzyl)-α-(3,3-diethoxy-1-propynyl)-3-pyridinemethanol there is obtained 2-(p-chloro-α-methylbenzyl)-2-(3-pyridyl)-3(2H)-furanone as orange colored crystals, m.p. 90°-100° C.;

α-ethynyl-α-(α-ethyl-2,4-dichlorobenzyl)3-pyridinemethanol there is obtained 4-(2,4-dichlorophenyl)-3-hydroxy-3-(3-pyridyl)-2-hexanone as colorless crystals, m.p. 171°-174° C.

Example 3

10.3 ml of a 1.4 molar solution of tert.butyl lithium in n-hexane are added dropwise to a solution of 2.2 ml of ethyl vinyl ether in 10 ml of tetrahydrofuran while cooling at −75° C. to −70° C. The reaction mixture is subsequently left to slowly warm to −5° C., during which the yellow-green suspension decolorizes to some extent and becomes clear. The mixture is again cooled to −70° C. to −75° C. and in this temperature range there is added dropwise thereto a solution of 4.0 g of 2-(2,4-dichlorophenyl)-1-(3-pyridyl)-4-pentyn-1-one in 14 ml of tetrahydrofuran. After 20 minutes at −75° C. the reaction mixture is left to warm to 0° C. For the working-up, the reaction mixture is treated with 100 ml of saturated aqueous sodium bicarbonate solution and extracted with ethyl acetate, and the organic phase is washed three times with saturated aqueous sodium chloride solution and evaporated under reduced pressure. The crude product is subsequently purified by column chromatography on silica gel with methylene chloride/ethyl acetate (1:1) and recrystallization from methylene chloride/n-hexane. In this manner there is obtained 1.0 g of α-(1-ethoxyvinyl)-α-[2,4-dichloro-α-(2-propynyl-benzyl]-3-pyridinemethanol, m.p. 139° C.

In an analogous manner, starting from 2,4-dichlorobenzyl 3-pyridyl ketone and methyl vinyl ether there is obtained α-(2,4-dichlorobenzyl)-α-(1-methoxyvinyl)-3-pyridinemethanol as colorless crystals, m.p. 138°-139° C.

2-(2,4-dichlorophenyl)-1-(3-pyridyl)-1-propanone and methyl vinyl ether there is obtained α-(2,4-dichloro-α-methylbenzyl)-α-(1-methoxyvinyl)-3-pyridinemethanol as colorless crystals, m.p. 140°-141° C.;

2-(2,4-dichlorophenyl)-1-(3-pyridyl)-4-penten-1-one and ethyl vinyl ether there is obtained α-(1-ethoxyvinyl)-α-(α-allyl-2,4-dichlorobenzyl)-3-pyridinemethanol as colorless crystals, m.p. 128°-129° C.;

2,4-dichlorobenzyl 3-pyridyl ketone and ethyl vinyl ether there is obtained α-(1-ethoxyvinyl)-α-(2,4-dichlorobenzyl)-3-pyridylmethanol as colorless crystals, m.p. 140°-141° C.;

2-(2,4-dichlorophenyl)-1-(3-pyridyl)-1-propanone and ethyl vinyl ether there is obtained α-(-ethoxyvinyl)-α-(2,4-dichloro-α-methylbenzyl)-3-pyridinemethanol as colorless crystals, m.p. 134°-136° C.;

2-(2,4-dichlorophenyl)-1-(3-pyridyl)-1-propanone and butyl vinyl ether there is obtained α-(butoxyvinyl)-α-(2,4-dichloro-α-methylbenzyl)-3-pyridinemethanol as colorless crystals, 115°-116° C.;

2-(2,4-dichlorophenyl)-1-(3-pyridyl)-1-propanone and isobutyl vinyl ether there is obtained α-(1-isobutoxyvinyl)-α-(2,4-dichloro-α-methylbenzyl)-3-pyridinemethanol as colorless crystals, m.p. 132°-133° C.;

2-(2,4-dichlorophenyl)-1-(3-pyridyl)-1-propanone and ethyl (1-propenyl)ether there is obtained α-(1-ethoxy-1-propenyl)-α-(2,4-dichloro-α-methylbenzyl)-3-pyridinemethanol as colorless crystals, m.p. 120°-121° C.;

2,4-dichlorobenzyl 3-pyridyl ketone and butyl vinyl ether there is obtained α-(1-butoxyvinyl)-α-(2,4-dichlorobenzyl)-3-pyridinemethanol as colorless crystals, m.p. 97° C.;

2,4-dichlorobenzyl 3-pyridyl ketone and isobutyl vinyl ether there is obtained α-(1-isobutoxyvinyl)-α-(2,4-dichlorobenzyl)-3-pyridinemethanol as colorless crystals, m.p. 107°-108° C.;

2-(2,4-dichlorophenyl)-1-(3-pyridyl)-1-pentanone and ethyl vinyl ether there is obtained α-(1-ethoxyvinyl)-α-(2,4-dichloro-α-propylbenzyl)-3-pyridinemethanol as colorless crystals, m.p. 133°-136° C.

EXAMPLE 4

A mixture of 2.0 g of α-(1-ethoxyvinyl)-α-[2,4-dichloro-α-(2-propynyl)-benzyl]-3-pyridinemethanol (see Example 3, 1st end product), 1 ml of concentrated hydrochloric acid and 15 ml of methanol as a clear yellow solution is held at room temperature for 1 hour. Thereafter, the mixture is evaporated under reduced pressure in order to remove methanol and the residue is neutralized with saturated aqueous sodium bicarbonate solution. The aqueous mixture is extracted with ethyl acetate and the organic phase is washed with saturated aqueous sodium chloride solution and evaporated. Finally, the residue is recrystallized from methylene chloride/n-hexane. There are obtained 1.8 g of 4-(2,4-dichlorophenyl)-3-hydroxy-3-(3-pyridyl)-6-heptyn-2-one, m.p. 132° C.

In an analogous manner, starting from
α-(1-ethoxyvinyl)-α-(α-allyl-2,4-dichlorobenzyl)-3-pyridinemethanol (see Example 3, 4th end product) there is obtained 4-(2,4-dichlorophenyl)-3-hydroxy-3-(3-pyridyl)-6-hepten-2-one as colorless crystals, m.p. 124°–125° C.

Example 5

1.2 g of 3-(2,4-dichlorophenyl)-2-(3-pyridyl)-1,2-butanediol are dissolved under argon in 19 ml of N,N-dimethylformamide and treated at −15° C. with 0.12 g of sodium hydride (99%). The mixture is left to come to 0° C. and stirred at this temperature for 6 hours and 0.4 ml of ethyl iodide is added thereto. There thereby results a red-orange colored suspension which, after stirring at 0° C. for 1 hour, is treated with 20 ml of saturated aqueous sodium bicarbonate solution and subsequently evaporated under a pressure of 0.1 mmHg in order to remove the solvent. The residue is taken up in water and the aqueous solution extracted with ethyl acetate, and the organic phase is washed with saturated aqueous sodium chloride solution and then evaporated to dryness under reduced pressure. The oily residue is purified by chromatography on silica gel with diethyl ether/n-hexane (17:3) and it is recrystallized from methylene chloride/n-hexane. In this manner there is obtained 0.7 g of α-ethoxymethyl-α-(2,4-dichloro-α-methylbenzyl)-3-pyridinemethanol as colorless crystals, m.p. 86° C.

In an analogous manner, starting from
3-(2,4-dichlorophenyl)-2-(3-pyridyl)-1,2-butanediol and methyl iodide there is obtained α-(2,4-dichloro-α-methylbenzyl)-α-methoxymethyl-3-pyridinemethanol as colorless crystals, m.p. 105°–107° C.;
4-(2,4-dichlorophenyl)-3-(3-pyridyl)-2,3-butanediol and methyl iodide there is obtained α-(2,4-dichlorobenzyl)-α-(1-methoxyethyl)-3-pyridinemethanol as colorless crystals, m.p. 94°–95° C.;
4-(2,4-dichlorophenyl)-3-(3-pyridyl)-2,3-hexanediol and methyl iodide there is obtained α-(α-ethyl-2,4-dichlorobenzyl)-α-(1-methoxyethyl)-3-pyridinemethanol as colorless crystals, m.p. 155° C.

Example 6

A mixture of 2.0 g of α-(2,4-dichlorobenzyl)-α-(1-methoxyvinyl)-3-pyridinemethanol (see Example 3, 2nd end product), 0.2 g of hydrogenation catalyst (5% palladium on carbon) and 40 ml of acetic acid is stirred for 7 hours at room temprature under a hydrogen atmosphere at normal pressure. Thereafter, the hydrogenation catalyst is removed by filtration, the filtrate is freed from solvent under reduced pressure, the residue is taken up in a saturated sodium bicarbonate solution and the solution is extracted with ethyl acetate. The organic phase is evaporated and the residue is crystallized from methylene chloride/n-hexane. In this manner there is obtained α-(2,4-dichlorobenzyl)-α-(1-methoxyethyl)-3-pyridinemethanol as colorless crystals, m.p. 94°–95° C.

Example 7

18.2 ml of a 1.4 molar solution of sec.butyl lithium in cyclohexane or added dropwise at −75° C. to a turbid solution of 2.86 g of freshly sublimed potassium tert.butanolate in 145 ml of tert.butyl methyl ether. The mixture is stirred at this temperature for 2 hours and subsequently treated with 25 ml of a 2 molar solution of lithium bromide in tetrahydrofuran. The temperature of the mixture is raised to −10° C. and after 30 minutes is again lowered to −75° C. Thereafter, a solution of 4.84 g of 2,4-dichlorobenzyl 3-pyridyl ketone in 28 ml of tetrahydrofuran is added dropwise thereto at −75° C., the reaction temperature is raised to 0° C. after 15 minutes and the reaction is completed by the cautious addition of 20 ml of saturated aqueous sodium bicarbonate solution. The mixture is diluted with 200 ml of water and extracted with ethyl acetate. In this manner there is obtained an educt/product mixture (about 2:1) which is separated by chromatography on silica gel into, inter alia, α-(tert.butoxymethyl)-α-(2,4-dichlorobenzyl)-3-pyridinemethanol as a colorless oil.

In an analogous manner, starting from
2,4-dichloro-α-methylbenzyl 3-pyridyl ketone and tert.butyl methyl ether there is obtained α-(tert.butoxymethyl)-α-(2,4-dichloro-α-methylbenzyl)-3-pyridinemethanol as colorless crystals, m.p. 123°–125° C.

Example 8

A solution of 1.5 g of 1-(2,4-dichloro-α-methylbenzyl)-1-hydroxy-1-(3-pyridyl)-2-butanone (see Example 1, 2nd end product) and 1.4 g of O-methylhydroxylamine hydrochloride in 10 ml of pyridine is heated at reflux temperature for 16 hours. The solution is subsequently partitioned between ethyl acetate and water and the aqueous phase is extracted three times with fresh amounts of ethyl acetate. The combined organic phases are washed with saturated aqueous sodium chloride solution, the solvent is removed by evaporation under reduced pressure and the residue is purified by column chromatography on silica gel with methylene chloride/ethyl acetate (4:1) and recrystallization from methylene chloride/n-hexane. This gives 1.3 g of colorless crystals of 5-(2,4-dichlorophenyl)-4-hydroxy-4-(3-pyridyl)-3-hexanone O-methyl oxime, m.p. 168°–170° C.

In an analogous manner, starting from
α-(2,4-dichlorobenzyl)-α-hydroxy-3-pyridineacetaldehyde (see Example 1, 5th end product) and O-methylhydroxylamine hydrochloride there is obtained α-(2,4-dichlorobenzyl)-3-pyridineglycol aldehyde (Z)-O-methyl oxime as colorless crystals, m.p. 134°–135° C.;
α-(2,4-dichloro-α-methylbenzyl)-α-hydroxy-3-pyridineacetaldehyde (see Example 1, 4th end product) and O-methylhydroxylamine hydrochloride there is obtained α-(2,4-dichloro-α-methylbenzyl)-α-[(E)-(methoxyimino)-methyl]-3-pyridinemethanol as colorless crystals, m.p. 147°–148° C.;
4-(2,4-dichlorobenzyl)-3-hydroxy-3-(3-pyridyl)-2-butanone (see Example 2, 4th end product) and hydroxylamine hydrochloride there is obtained 4-(2,4-dichlorobenzyl)-3-hydroxy-3-pyridyl)-2-butanone oxide as colorless crystals, m.p. 174°–178° C.;

4-(2,4-dichlorobenzyl)-3-hydroxy-3-(3-pyridyl)-2-butanone (see Example 2, 4th end product) and O-methylhydroxylamine hydrochloride there is obtained 4-(2,4-dichlorobenzyl)-3-hydroxy-3-(3-pyridyl)-2-butanone O-methyl oxime as colorless crystals, m.p. 136°–138° C.;

4-(2,4-dichlorophenyl)-3-hydroxy-3-(3-pyridyl)-2-pentanone (see Example 2, 3rd end product) and hydroxylamine hydrochloride there is obtained 4-(2,4-dichlorophenyl)-3-hydroxy-3-(3-pyridyl)-2-pentanone oxime as colorless crystals, m.p. 174°–175° C.;

4-(2,4-dichlorophenyl)-3-hydroxy-3-(3-pyridyl)-2-pentanone (see Example 2, 3rd end product) and O-methylhydroxylamine hydrochloride there is obtained 4-(2,4-dichlorophenyl)-3-hydroxy-3-(3-pyridyl)-2-pentanone O-methyl oxime as colorless crystals, m.p. 154°–157° C.;

α-(2,4-dichloro-α-methylbenzyl)-α-hydroxy-3-pyridineacetaldehyde (see Example 1, 4th end product) and hydroxylamine hydrochloride there is obtained α-(2,4-dichloro-α-methylbenzyl)-3-pyridineglycol aldehyde oxime as colorless crystals, m.p. 185°–186° C.;

4-(2,4-dichlorophenyl)-3-hydroxy-3-(3-pyridyl)-2-hexanone (see Example 2, 10th end product) and hydroxylamine hydrochloride there is obtained 4-(2,4-dichlorophenyl)-3-hydroxy-3-(3-pyridyl)-2-hexanone oxime as colorless crystals, m.p. 196°–199° C.

Example 9

27 ml of ethylene glycol and 0.8 ml of concentrated sulphuric acid are added to a solution of 5 g of 5-(2,4-dichlorophenyl)-4-hydroxy-4-(3-pyridyl)-3-pentanone (see Example 1, 3rd end product) in 90 ml of toluene and the reaction mixture is heated at reflux temperature for 24 hours on a water separator. After cooling to room temperature the mixture is neutralized with saturated aqueous sodium bicarbonate solution and extracted with ethyl acetate. The organic phase is washed with saturated aqueous sodium chloride solution, the solvent is removed by evaporation under reduced pressure and the residue is recrystallized from methylene chloride/n-hexane. In this manner there are obtained 5.3 g of 5-(2,4-dichlorophenyl)-4-hydroxy-4-(3-pyridyl)-2-pentanone ethylene ketal as colorless crystals, m.p. 136°–137° C.

In an analogous manner, starting from
α-(2,4-dichlorobenzyl)-α-hydroxy-3-pyridineacetaldehyde (see Example 1, 5th end product) and ethylene glycol there is obtained α-(2,3-dichlorobenzyl)-α-(1,3-dioxolan-2-yl)-3-pyridinemethanol as colorless crystals, m.p. 120°–121° C.;

4-(2,4-dichlorophenyl)-3-hydroxy-3-(3-pyridyl)-2-butanone (see Example 2, 4th end product) and ethylene glycol there is obtained 4-(2,4-dichlorophenyl)-3-hydroxy-3-(3-pyridyl)-2-butanone ethylene ketal as colorless crystals, m.p. 126°–127° C.;

4-(2,4-dichlorophenyl)-3-hydroxy-3-(3-pyridyl)-2-pentanone (see Example 2, 3rd end product) ethylene glycol there is obtained 4-(2,4-dichlorophenyl)-3-hydroxyl-3-(3-pyridyl)-2-pentanone ethylene ketal as colorless crystals, m.p. 142°–144° C.;

4-(2,4-dichlorophenyl)-3-hydroxy-3-(3-pyridyl)-2-butanone (see Example 2, 4th end product) and propane-1,3-diol there is obtained 4-(2,4-dichlorophenyl)-3-hydroxy-3-(3-pyridyl)-2-butanone trimethylene ketal as colorless crystals, m.p. 161° C.

Example 10

A solution of 4.9 g of 4-(2,4-dichlorophenyl)-3-(3-pyridyl)-2,3-pentanediol in 400 ml of methylene chloride and 100 ml of tetrahydrofuran is treated with 5.3 g of O-amino-2,4,6-trimethylbenzenesulphonate and the reaction mixture is stirred at room temperature for 18 hours. Thereafter, the solvent is removed by evaporation under reduced pressure and the residue is purified by chromatograhy on silica gel with methylene chloride/ethanol (3:2). There are obtained 3.1 g of 1-amino-3-[2,4-dichloro-α-hydroxy-α-(1-hydroxyethyl)-β-methylphenethyl]-pyridinium 2,4,6-trimethylbenzenesulphonate as a colorless oil.

In an analogous manner, starting from
4-(2,4-dichlorobenzyl)-3-hydroxy-3-(3-pyridyl)-2-butanone (see Example 2, 4th end product) there is obtained 3-(α-acetyl-2,4-dichloro-α-hydroxyphenethyl)-1-aminopyridinium 2,4,6-trimethylbenzenesulphonate as a colorless oil.

II. PRODUCTION OF THE STARTING MATERIALS OF FORMULAE II AND VI

Example 11

38.8 ml of a 1.6 molar solution of n-butyl lithium in n-hexane are added dropwise to a solution of 9.2 g of 2-isopropyl-1,3-dithiane in 150 ml of tetrahydrofuran while cooling at −75° C. to −70° C. Subsequently, the yellow solution is left to warm slowly to 0° C., stirred at this temperature for 10 minutes and again cooled to −70° C. to −75° C. There is then dropwise thereto within this temperature range during 45 minutes a solution of 15 g of 2,4-dichlorobenzyl (3-pyridyl) ketone in 40 ml of tetrahydrofuran and the reaction mixture is left to warm slowly to room temperature. The reaction is completed by adding 40 ml of water, the solvent is removed by evaporation under reduced pressure and the residue is taken up in diethyl ether. The ethereal solution is then washed three times with saturated aqueous sodium chloride solution, the organic phase is evaporated under reduced pressure and the residue is purified by chromatography on silica gel with diethyl ether/n-hexane (1:1). In this manner there are obtained 8.7 g of crystalline α-(2,4-dichlorobenzyl)-α-(2-isopropyl-m-dithianyl-2)-3-pyridinemethanol, m.p. 124°–126° C.

In an analogous manner, starting from
2-ethyl-1,3-dithiane, n-butyl lithium and 2-(2,4-dichlorophenyl)-1-(3-pyridyl)-1-propanone there is obtained α-(2-ethyl-m-dithianyl-2)-α-(2,4-dichloro-α-methylbenzyl)-3-pyridinemethanol as colorless crystals, m.p. 100°–101° C.;

2-ethyl-1,3-dithiane, n-butyl lithium and 2,4-dichlorobenzyl (3-pyridyl) ketone there is obtained α-(2-ethyl-m-dithianyl-2)-α-(2,4-dichlorobenzyl)-3-pyridinemethanol as colorless crystals, m.p. 138°–139° C.;

1,3-dithiane, n-butyl lithium and 2-(2,4-dichlorophenyl)-1-(3-pyridyl)-1-propanone there is obtained α-(2,4-dichloro-α-methylbenzyl)-α-(m-dithianyl-2)-3-pyridinemethanol as colorless crystals, m.p. 124°–127° C.

1,3-dithiane, n-butyl lithium and 2,4-dichlorobenzyl 3-(3-pyridyl)ketone there is obtained α-(m-dithianyl-1)-3-pyridinemethanol as yellow crystals, m.p. 142°–144° C.

Example 12

A solution of 5.8 g of 4-(2,4-dichlorophenyl)-3-hydroxy-3-(3-pyridyl)-6-heptyn-2-one (see Example 4, 1st end product) in 100 ml of ethanol is treated at room temperature with 0.8 g of sodium borohydride and the mixture is stirred for 30 minutes. Thereafter, the excess sodium borohydride is destroyed by adjusting the yellowish reaction solution to pH 1 with 2N sulphuric acid and the mixture is again neutralized with saturated aqueous sodium bicarbonate solution. The mixture is evaporated under reduced pressure in order to remove the solvent, the residue is partitioned between ethyl acetate and water and the organic phase is washed with saturated aqueous sodium chloride solution and evaporated under reduced pressure in order to remove the solvent. The residue is purified by chromatography on silica gel with methylene chloride/ethyl acetate (3:7). In this manner there are obtained 5.7 g of 4-(2,4-dichlorophenyl)-3-(3-pyridyl)-6-heptyne-2,3-diol as a colorless solid foam. In an analogous manner, starting from 4-(2-dichlorophenyl)-3-hydroxy-3-(3-pyridyl)-2-pentanone (see Example 2, 3rd end product) there is obtained 4-(2,4-dichlorophenyl)-3-(3-pyridyl)-2,3-pentanediol as colorless crystals, m.p. 90°–110° C.;

4-(2,4-dichlorophenyl)-3-hydroxy-3-(3-pyridyl)-2-butanone (see Example 2, 4th end product) there is obtained 4-(2,4-dichlorophenyl)-3-(3-pyridyl)-2,3-butanediol as colorless crystals, m.p. 165°–167° C.;

4-(2,4-dichlorophenyl)-3-hydroxy-3-(3-pyridyl)-2-heptanone (see Example 2, 5th end product) there is obtained 4-(2,4-dichlorophenyl)-3-(3-pyridyl)-2,3-heptanediol as colorless crystals, m.p. 202°–204° C.;

α-(2,4-dichlorobenzyl)-α-hydroxy-3-pyridineacetaldehyde (see Example 1, 5th end product) there is obtained 1-(2,4-dichlorobenzyl)-1-(3-pyridyl)-1,2-ethanediol as colorless crystals m.p. 158°–159° C.;

1-(2,4-dichloro-α-methylbenzyl)-1-hydroxy-1-(3-pyridyl)-2-butanone (see Example 1, 2nd end product) there is obtained 5-(2,4-dichlorophenyl-4-(3-pyridyl)-3,4-hexanediol as a colorless solid foam;

4-(2,4-dichlorophenyl)-3-hydroxy-3-(3-pyridyl)-6-hepten-2-one (see Example 4, 2nd end product) there is obtained 4-(2,3-dichlorophenyl)-3-(3-pyridyl)-6-hepten-2,3-diol as colorless crystals, m.p. 190° C.;

α-(2,4-dichloro-α-methylbenzyl)-α-hydroxy-3-pyridineacetaldehyde (see Example 1, 4th end product) there is obtained 3-(2,4-dichlorophenyl)-2-(3-pyridyl)-1,2-butanediol as colorless crystals, m.p. 131°–132° C.

4-(2,4-dichlorophenyl)-3-hydroxy-3-(3-pyridyl)-2-hexanone (see Example 2, 10th end product) there is obtained 4-(2,4-dichlorophenyl)-3-(3-pyridyl)-2,3-hexanediol as colorless crystals, m.p. 172°–175° C.

III. Formulation Examples:

Example 13

A emulsifiable concentrate has the following composition:

|  | g/liter |
|---|---|
| Active substance of formula I | 250 |
| Polyarylphenol-(18) ethoxylate (emulsifier) | 300 |
| N—Methyl-2-pyrrolidone (solvent) ad | 1 l |

The active substance and the emulsifier are taken up in the solvent, whereby a clear solution results which is resistant to cold. When poured into water it gives a practically clear emulsion which serves as a spray liquor.

What is claimed:

1. A compound of the formula

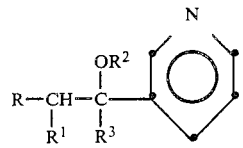

wherein R is mono-, di- or trisubstituted phenyl, wherein the substituents are the same or different and are selected from the group consisting of 1 to 3 halogen atoms, 1 or 2 $C_{1-3}$-alkyl groups, 1 or 2 $C_{1-3}$-alkoxy groups and 1 or 2 trifluoromethyl groups; $R^1$ is hydrogen, $C_{1-6}$-alkyl, $C_{2-6}$-alkenyl or $C_{2-6}$-alkynyl; $R^2$ is hydrogen; $R^3$ i selected from the group consisting of —CO—$R^4$, —C(O$R^5$)=CH$R^6$, —CH($R^4$)O$R^5$, —C($R^4$)=NO$R^7$ and

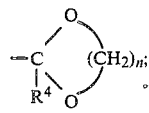

$R^4$ is hydrogen or $C_{1-5}$-alkyl; $R^5$ is $C_{1-4}$-alkyl; $R^6$ and $R^7$ are hydrogen or $C_{1-4}$-alkyl; n is 2 or 3; or $R^2$ taken together with $R^4$ is equal to —CH=CH—; as well as the N-amino salts and acid addition salts thereof.

2. A compound according to claim 1, wherein R is mono- or dihalophenyl.

3. A compound according to claim 2, wherein R is mono- or dichlorophenyl.

4. A compound according to claim 3, wherein R is 2,4-dichlorophenyl.

5. A compound according to claim 2, wherein $R^1$ is hydrogen or $C_{1-6}$-alkyl.

6. A compound according to claim 5, wherein $R^2$ is hydrogen.

7. A compound according to claim 6, wherein $R^3$ is —CO$R^4$ or —C(O$R^5$)=CH$R^6$.

8. A compound according to claim 7 wherein $R^3$ is acetyl, 1-methoxyvinyl or 1-ethoxyvinyl.

9. A compound according to claim 1, which is selected from the group consisting of 5-(2,4-dichlorophenyl)-4-hydroxy-4-(3-pyridyl)-3-pentanone, 2-(2,4-dichloro-α-methylbenzyl)-2-(3-pyridyl)-3(2H)-furanone, 2-(2,4-dichlorobenzyl)-2-(3-pyridyl)-3(2H)-furanone, 4-(2,4-dichlorophenyl)-3-hydroxy-3-(3-pyridyl)-2-pentanone, 4-(2,4-dichlorophenyl)-3-hydroxy-3-(3-pyridyl)-2-butanone, 4-(p-chlorophenyl)-3-hydroxy-3-(3-pyridyl)-2-pentanone, α-(2,4-dichlorobenzyl)-α-(1-methoxyvinyl)-3-pyridinemethanol, α-ethoxymethyl-α-(2,4-dichloro-α-methylbenzyl)-3-pyridinemethanol, α-(2-4-dichloro-α-methylbenzyl)-α-methoxymethyl-3-pyridinemethanol, α-(2,4-dichlorobenzyl)-α-(1-methoxyethyl)-3-pyridinemethanol, α-(2,4-dichlorobenzyl)-3-pyridineglycol aldehyde O-methyl oxime and α-(2,4-dichloro-α-methylbenzyl)-α-[(methoxyimino)methyl]-3-pyridinemethanol.

10. A compound according to claim 1, selected from the group consisting of
5-(2,4-dichlorophenyl)-4-hydroxy-2-methyl-4-(3-pyridyl)-3-pentanone,
1-(2,4-dichloro-α-methylbenzyl)-1-hydroxy-1-(3-pyridyl)-2-butanone,
α-(2,4-dichloro-α-methylbenzyl)-α-hydroxy-3-pyridineacetaldehyde,
α-(2,4-dichlorobenzyl)-α-hydroxy-3-pyridineacetaldehyde,
4-(2,4-dichlorophenyl)-3-hydroxy-3-(3-pyridyl)-2-heptanone,
2-(2,4-dichloro-α-propylbenzyl)-2-(3-pyridyl)-3(2H)furanone,
4-(p-chlorophenyl)-3-hydroxy-3-(3-pyridyl)-2-butanone,
2-(p-chloro-α-methylbenzyl)-2-(3-pyridyl)-3(2H)-furanone,
α-(1-ethoxyvinyl)-α-[2,4-dichloro-α-(2-propynyl)-benzyl]-3-pyridinemethanol,
α-(2,4-dichloro-α-methylbenzyl)-α-(1-methoxyvinyl)-3-pyridinemethanol,
α-(1-ethoxyvinyl)-α-(α-allyl-2,4-dichlorobenzyl)-3-pyridinemethanol,
α-(1-ethoxyvinyl)-α-(2,4-dichlorobenzyl)-3-pyridinemethanol,
α-(1-ethoxyvinyl)-α-(2,4-dichloro-α-methylbenzyl)-3-pyridinemethanol,
α-(1-butoxyvinyl)-α-(2,4-dichloro-α-methylbenzyl)-3-pyridinemethanol,
α-(1-isobutoxyvinyl)-α-(2,4-dichloro-α-methylbenzyl)-3-pyridinemethanol,
α-(1-ethoxy-1-propenyl)-α-(2,4-dichloro-α-methylbenzyl)-3-pyridinemethanol,
α-(1-butoxyvinyl)-α-(2,4-dichlorobenzyl)-3-pyridinemethanol,
α-(1-isobutoxyvinyl)-α-(2,4-dichlorobenzyl)-3-pyridinemethanol,
α-(1-ethoxyvinyl)-α-(2,4-dichloro-α-propylbenzyl)-3-pyridinemethanol,
4-(2,4-dichlorophenyl)-3-hydroxy-3-(3-pyridyl)-6-heptyn-2-one,
4-(2,4-dichlorophenyl)-3-hydroxy-3-(3-pyridyl)-6-hepten-2-one,
5-(2,4-dichlorophenyl)-4-hydroxy-4-(3-pyridyl)-3-hexanone O-methyl oxime,
4-(2,4-dichlorobenzyl)-3-hydroxy-3-(3-pyridyl)-2-butanone oxime,
4-(2,4-dichlorobenzyl)-3-hydroxy-3-(3-pyridyl)-2-butanone O-methyl oxime,
4-(2,4-dichlorophenyl)-3-hydroxy-3-(3-pyridyl)-2-pentanone oxime,
4-(2,4-dichlorophenyl)-3-hydroxy-3-(3-pyridyl)-2-pentanone O-methyl oxime,
α-(2,4-dichloro-α-methylbenzyl)-3-pyridineglycol aldehyde oxime,
5-(2,4-dichlorophenyl)-4-hydroxy-4-(3-pyridyl)-2-pentanone ethylene ketal,
α-(2,3-dichlorobenzyl)-α-(1,3-dioxolan-2-yl)-3-pyridinemethanol,
4-(2,4-dichlorophenyl)-3-hydroxy-3-(3-pyridyl)-2-butanone ethylene ketal,
4-(2,4-dichlorophenyl)-3-hydroxy-3-(3-pyridyl)-2-pentanone ethylene ketal,
1-amino-3-[2,4-dichloro-α-hydroxy-α-(1-hydroxyethyl)-β-methylphenethyl]-pyridinium 2,4,6-trimethylbenzenesulphonate and
3-(α-acetyl-2,4-dichloro-α-hydroxyphenethyl)-1-aminopyridinium 2,4,6-trimethylbenzenesulphonate.

11. A compound according to claim 1, selected from the group consisting of
4-(2,4-dichlorophenyl)-3-hydroxy-3-(3-pyridyl)-2-hexanone,
α-(α-ethyl-2,4-dichlorobenzyl)-α-(1-methoxyethyl)-3-pyridinemethanol,
α-(tert.butoxymethyl)-α-(2,4-dichlorobenzyl)-3-pyridinemethanol,
α-(tert.butoxymethyl)-α-(2,4-dichloro-α-methylbenzyl)-3-pyridinemethanol,
4-(2,4-dichlorophenyl)-3-hydroxy-3-(3-pyridyl)-2-hexanone oxime and
4-(2,4-dichlorophenyl)-3-hydroxy-3-(3-pyridyl)-2-butanone trimethylene ketal.

12. A compound of the formula

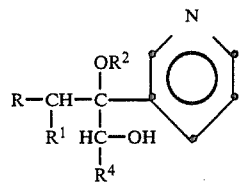

VI wherein R is mono-, di- or trisubstituted phenyl, wherein the substituents are the same or different and are selected from the group consisting of 1 to 3 halogen atoms, 1 or 2 $C_{1-3}$-alkyl groups, 1 or 2 $C_{1-3}$-alkoxy groups and 1 or 2 trifluoromethyl groups; $R^1$ is hydrogen, $C_{1-6}$-alkyl, $C_{2-6}$-alkenyl or $C_{2-6}$-alkylnyl; $R^2$ is hydrogen; $R^4$ is hydrogen or $C_{1-5}$-alkyl; or $R^2$ taken together with $R^4$ is —CH=CH—.

13. A compound according to claim 12, selected from the group consisting of
4-(2,4-dichlorophenyl)-3-(3-pyridyl)-2,3-butanediol,
1-(2,4-dichlorobenzyl)-1-(3-pyridyl)-1,2-ethanediol,
5-(2,4-dichlorophenyl)-4-(3-pyridyl)-3,4-hexanediol,
3-(2,4-dichlorophenyl)-2-(3-pyridyl)-1,2-butanediol,
4-(2,4-dichlorophenyl)-3-(3-pyridyl)-6-heptyne-2,3-diol,
4-(2,4-dichlorophenyl)-3-(3-pyridyl)-2,3-pentanediol and
4-(2,4-dichlorophenyl)-3-(3-pyridyl)-6-heptene-2,3-diol.

14. A compound according to claim 12 which is 4-(2,4-dichlorophenyl)-3-(3-pyridyl)-2,3-hexane-diol.

15. A fungicidal comprising as the active agent a compound of the formula

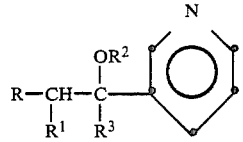

I wherein R is mono-, di- or trisubstituted phenyl, wherein the substituents are the same or different and are selected from the group consisting of 1 to 3 halogen atoms, 1 or 2 $C_{1-3}$-alkyl groups, 1 or 2 $C_{1-3}$-alkoxy groups and 1 or 2 trifluoromethyl groups; $R^1$ is hydrogen, $C_{1-6}$-alkyl, $C_{2-6}$-alkenyl or $C_{2-6}$-alkynyl; $R^2$ is hydrogen; $R^3$ is selected from the group consisting of —CO—R⁴, —C(OR⁵)=CHR⁶, —CH(R⁴)OR⁵, —C(R⁴)=NOR⁷ and

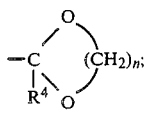

R⁴ is hydrogen or C₁₋₅-alkyl; R⁵ is C₁₋₄-alkyl; R⁶ and R⁷ are hydrogen or C₁₋₄-alkykl; n is equal to 2 or 3; or R² taken together with R⁴ is equal to —CH=CH—; or an N-amino salt or acid addition salt thereof, and formulation adjuvants.

16. A composition according to claim 15, wherein said formulation adjuvants are selected from the group consisting of solid carrier substances, solvents, dispersion media, tensides, dispersing agents without tenside action and stabilizers.

17. A composition according to claim 16, wherein the active agent is selected from the group consisting of
5-(2,4-dichlorophenyl)-4-hydroxy-4-(3-pyridyl)-3-pentanone,
2-(2,4-dichloro-α-methylbenzyl)-2-(3-pyridyl)-3(2H)-furanone,
2-(2,4-dichlorobenzyl)-2-(3-pyridyl)-3(2H)-furanone,
4-(2,4-dichlorophenyl)-3-hydroxy-3-(3-pyridyl)-2-pentanone,
4-(2,4-dichlorophenyl)-3-hydroxy-3-(3-pyridyl)-2-butanone,
4-(p-chlorophenyl)-3-hydroxy-3-(3-pyridyl)-2-pentanone,
α-(2,4-dichlorobenzyl)-α-(1-methoxyvinyl)-3-pyridinemethanol,
α-ethoxymethyl-α-(2,4-dichloro-α-methylbenzyl)-3-pyridinemethanol,
α-(2-4-dichloro-α-methylbenzyl)-α-methoxymethyl-3-pyridinemethanol,
α-(2,4-dichlorobenzyl)-α-(1-methoxyethyl)-3-pyrdine methanol,
α-(2,4-dichlorobenzyl)-3-pyridineglycol aldehyde O-methyl oxime and
α-(2,4-dichloro-α-methylbenzyl)-α-[(methoxyimino)-methyl]-3-pyridinemethanol as well as formulation adjuvants.

18. A fungicidal composition comprising a fungicidally active agent which is a compound selected from the group consisting of
4-(2,4-dichlorophenyl)-3-(3-pyridyl)-2,3-butanediol,
1-(2,4-dichlorobenzyl)-1-(3-pyridyl)-1,2-ethanediol,
5-(2,5-dichlorophenyl)-4-(3-pyridyl)-3,4-hexanediol,
3-(2,4-dichlorophenyl)-2-(3-pyridyl)-1,2-butanediol,
4-(2,4-dichlorophenyl)-3-(3-pyridyl)-6-heptyne-2,3-diol,
4-(2,4-dichlorophenyl)-3-(3-pyridyl)-2,3-pentanediol,
4-(2,4-dichlorophenyl)-3-(3-pyridyl)-6-heptene-2,3-diol and
4-(2,4-dichlorophenyl)-3-(3-pyridyl)-2,3-hexanediol
as well as formulation adjuvants.

19. A method for controlling the growth of an undesirable phytopathogenic fungus which method comprises applying to the locus to be protected an effective phytopathogenic fungus controlling amount of a compound of the formula

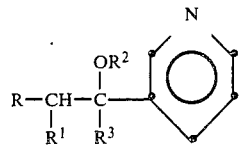

wherein R is mono-, di- or trisubstituted phenyl, wherein the substituents are the same or different and are selected from the group consisting of 1 to 3 halogen atoms, 1 or 2 C₁₋₃-alkyl groups, 1 or 2 C₁₋₃-alkoxy groups and 1 or 2 trifluoromethyl groups; R¹ is hydrogen, C₁₋₆-alkyl, C₂₋₆-alkenyl or C₂₋₆-alkynyl; R² is hydrogen; R³ is selected from the group consisting of —CO—R⁴, —C(OR⁵)=CHR⁶, —CH(R⁴)OR⁵, —C(R⁴)=NOR⁷ and

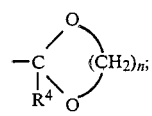

R⁴ is hydrogen or C₁₋₅-alkyl; R⁵ is C₁₋₄-alkyl; R⁶ and R⁷ are hydrogen or C₁₋₄-alkyl; n is 2 or 3; or R² taken together with R⁴ is equal to —CH=CH—; as well as the N-amino salts and acid addition salts thereof.

20. A method according to claim 19, wherein said phytopathogenic fungus is a member of the taxonomic class selected from the group consisting of Deuteromycetes, Ascomycetes and Basidiomycetes.

21. A method according to claim 19, wherein said phytopathogenic fungus is a member of the genus Botrytis, Erysiphe, Uncinula, Podosphaera, Venturia, Cercospora, Mycosphaerella, Sphaerotheca, Puccinia, Uromyces, Hemileia, Rhizoctonia, Alternaria, Cercosporella, Ceratocystis, Verticullium, Fusarium, Helminthosporium, Sclerotinia, Penicillium, Septona, Ustilago, Tilletia, Coniophora, Gloeophyllum and Aureobasidium.

22. A method according to claim 21, wherein said phytopathogenic fungus is *Botrytis cinerea, Erysiphe cichoracearum, Erysiphe graminis, Uncinula necator, Podosphaera leucotricha, Venturia inaequalis, Cercospora archidicola, Cercospora beticola* or *Mycosphaerella fijiensis*.

23. A method according to claim 19 wherein said locus to be protected is a plant, plant part, or the soil in which the plant is growing.

24. A method according to claim 19, wherein said locus to be protected is a plant seed or soil in which said seed is planted.

25. A method according to claim 19, wherein in said compound R is mono- or dihalophenyl, R¹ is hydrogen or C₁₋₆-alkyl and R³ is —COR⁴ or —C(OR⁵)=CHR⁶.

26. A method according to claim 25, wherein in said compound R is 2,4-dichlorophenyl, R¹ is hydrogen or methyl, R² is hydrogen and R³ is acetyl, 1-methoxyvinyl or 1-ethoxyvinyl.

27. A method according to claim 19, wherein said compound is selected from the group consisting of
5-(2,4-dichlorophenyl)-4-hydroxy-4-(3-pyridyl)-3-pentanone,
2-(2,4-dichloro-α-methylbenzyl)-2-(3-pyridyl)-3(2H)-furanone,
2-(2,4-dichlorobenzyl)-2-(3-pyridyl)-3(2H)-furanone, 4-(2,4-dichlorophenyl)-3-hydroxy-3-(3-pyridyl)-2-pentanone,
4-(2,4-dichlorophenyl)-3-hydroxy-3-(3-pyridyl)-2-butanone,
4-(p-chlorophenyl)-3-hydroxy-3-(3-pyridyl)-2-pentanone,
α-(2,4-dichlorobenzyl)-α-(1-methoxyvinyl)-3-pyridinemethanol,
α-ethoxymethyl-α-(2,4-dichloro-α-methylbenzyl)-3-pyridinemethanol,
α-(2-4-dichloro-α-methylbenzyl)-α-methoxymethyl-3-pyridinemethanol,
α-(2,4-dichlorobenzyl)-α-(1-methoxyethyl)-3-pyridinemethanol,
α-(2,4-dichlorobenzyl)-3-pyridineglycol aldhehyde O-methyl oxime and
α-(2,4-dichloro-α-methylbenzyl)-α[(methoxyimino)methyl]-3-pyridinemethanol.

28. A method according to claim 19, wherein said compound is selected from the group consisting of
5-(2,4-dichlorophenyl)-4-hydroxy-2-methyl-4-(3-pyridyl)-3-pentanone,
1-(2,4-dichloro-α-methylbenzyl)-1-hydroxy-1-(3-pyridyl)-2-butanone,
α-(2,4-dichloro-α-methylbenzyl)-α-hydroxy-3-pyridineacetaldehyde,
α-(2,4-dichlorobenzyl)-α-hydroxy-3-pyridineacetaldehyde,
4-(2,4-dichlorophenyl)-3-hydroxy-3-(3-pyridyl)-2-heptanone,
2-(2,4-dichloro-α-propylbenzyl)-2-(3-pyridyl)-3(2H)-furanone,
4-(p-chlorophenyl)-3-hydroxy-3-(3-pyridyl)-2-butanone,
2-(p-chloro-α-methylbenzyl)-2-(3-pyridyl)-3(2H)-furanone,
α-(1-ethoxyvinyl)-α-[2,4-dichloro-α-(2-propynyl)-benzyl]-3-pyridinemethanol,
α-(2,4-dichloro-α-methylbenzyl)-α-(1-methoxyvinyl)-3-pyridinemethanol,
α-(1-ethoxyvinyl)-α-(α-allyl-2,4-dichlorobenzyl)-3-pyridinemethanol,
α-(1-ethoxyvinyl)-α-(2,4-dichlorobenzyl)-3-pyridinemethanol,
α-(1-ethoxyvinyl)-α-(2,4-dichloro-α-methylbenzyl)-3-pyridinemethanol,
α-(1-butoxyvinyl)-α-(2,4-dichloro-α-methylbenzyl)-3-pyridinemethanol,
α-(1-isobutoxyvinyl)-α-(2,4-dichloro-α-methylbenzyl)-3-pyridinemethanol,
α-(1-ethoxy-1-propenyl)-α-(2,4-dichloro-α-methylbenzyl)-3-pyridinemethanol,
α-(1-butoxyvinyl)-α-(2,4-dichlorobenzyl)-3-pyridinemethanol,
α-(1-isobutoxyvinyl)-α-(2,4-dichlorobenzyl)-3-pyridinemethanol,
α-(1-ethoxyvinyl)-α-(2,4-dichloro-α-propylbenzyl)-3-pyridinemethanol,
4-(2,4-dichlorophenyl)-3-hydroxy-3-(3-pyridyl)-6-heptyn-2-one,
4-(2,4-dichlorophenyl)-3-hydroxy-3-(3-pyridyl)-6-hepten-2-one,
5-(2,4-dichlorophenyl)-4-hydroxy-4-(3-pyridyl)-3-hexanone O-methyl oxime,
4-(2,4-dichlorobenzyl)-3-hydroxy-3-(3-pyridyl)-2-butanone oxime,
4-(2,4-dichlorobenzyl)-3-hydroxy-3-(3-pyridyl)-2-butanone O-methyl oxime,
4-(2,4-dichlorophenyl)-3-hydroxy-3-(3-pyridyl)-2-pentanone oxime,
4-(2,4-dichlorophenyl)-3-hydroxy-3-(3-pyridyl)-2-pentanone O-methyl oxime,
α-(2,4-dichloro-α-methylbenzyl)-3-pyridineglycol aldehyde oxime,
5-(2,4-dichlorophenyl)-4-hydroxy-4-(3-pyridyl)-2-pentanone ethylene ketal,
α-(2,3-dichlorobenzyl)-α-(1,3-dioxolan-2-yl)-3-pyridinemethanol,
4-(2,4-dichlorophenyl)-3-hydroxy-3-(3-pyridyl)-2-butanone ethylene ketal,
4-(2,4-dichlorophenyl)-3-hydroxy-3-(3-pyridyl)-2-pentanone ethylene ketal,
1-amino-3-[2,4-dichloro-α-hydroxy-α-(1-hydroxyethyl)-β-methylphenethyl]-pyridinium 2,4,6-trimethylbenzenesulphonate,
3-(α-acetyl-2,4-dichloro-α-hydroxyphenethyl)-1-aminopyridinium 2,4,6-trimethylbenzenesulphonate,
4-(2,4-dichlorophenyl)-3-hydroxy-3-(3-pyridyl)-2-hexanone,
α-(α-ethyl-2,4-dichlorobenzyl)-α-(1-methoxyethyl)-3-pyridinemethanol,
α-(tert.butoxymethyl)-α-(2,4-dichlorobenzyl)-3-pyridinemethanol,
α-(tert.butoxymethyl)-α-(2,4-dichloro-α-methylbenzyl)-3-pyridinemethanol,
4-(2,4-dichlorophenyl)-3-hydroxy-3-(3-pyridyl)-2-hexanone oxime and
4-(2,4-dichlorophenyl)-3-hydroxy-3-(3-pyridyl)-2-butanone trimethylene ketal.

* * * * *